United States Patent [19] [11] 4,386,126
Turner [45] May 31, 1983

[54] ARTICLE FOR MAKING A SUN VISOR AND FAN

[76] Inventor: Patricia K. Turner, 1710 Treehouse, Plano, Tex. 75023

[21] Appl. No.: 297,246

[22] Filed: Aug. 28, 1981

[51] Int. Cl.³ .............................................. B65D 65/28
[52] U.S. Cl. ........................................ 428/43; 2/12; 2/197; D3/1; 416/70 A
[58] Field of Search ..................... 428/43; 2/12, 197; D3/1; 416/70 A

[56] References Cited

U.S. PATENT DOCUMENTS

| | | | |
|---|---|---|---|
| 797,143 | 8/1905 | Newlin | 2/11 |
| 1,499,490 | 7/1924 | Weil | 416/70 A |
| 2,052,180 | 8/1936 | Klie | 416/70 A |
| 2,521,017 | 9/1950 | Moen et al. | 2/197 X |
| 2,679,047 | 5/1954 | Bozzi | 428/43 X |
| 3,025,964 | 3/1962 | Summers et al. | 428/116 X |
| 3,969,837 | 7/1976 | Kresse | 428/16 X |
| 4,247,957 | 2/1981 | Rogers | 2/12 |

Primary Examiner—George F. Lesmes
Assistant Examiner—E. Rollins Buffalow
Attorney, Agent, or Firm—Sigalos & Levine

[57] ABSTRACT

An article of manufacture includes a piece of paper having rounded corners and an interiorly perforated area to be torn or removed from the paper. Upon such removal of the interior area, the interior area removed can be used as a fan when a stick or handle is attached to it and the outside area can be used as a sun visor. The outside area has a plurality of interfitting cuts so that the visor can be adjusted in size for the comfort of the user.

6 Claims, 3 Drawing Figures

U.S. Patent  May 31, 1983  4,386,126
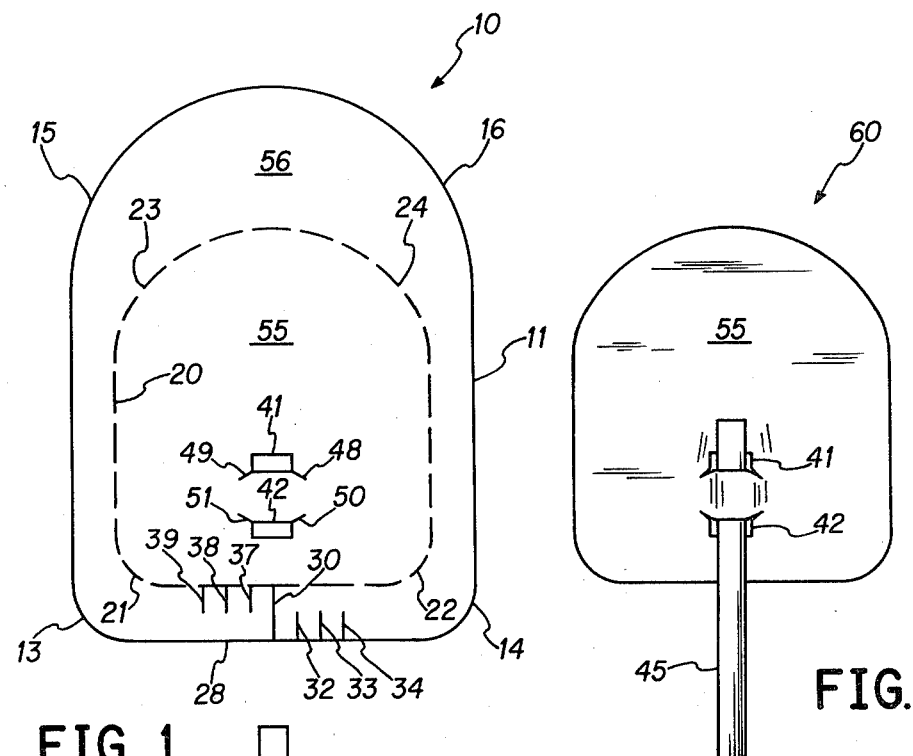
FIG. 1
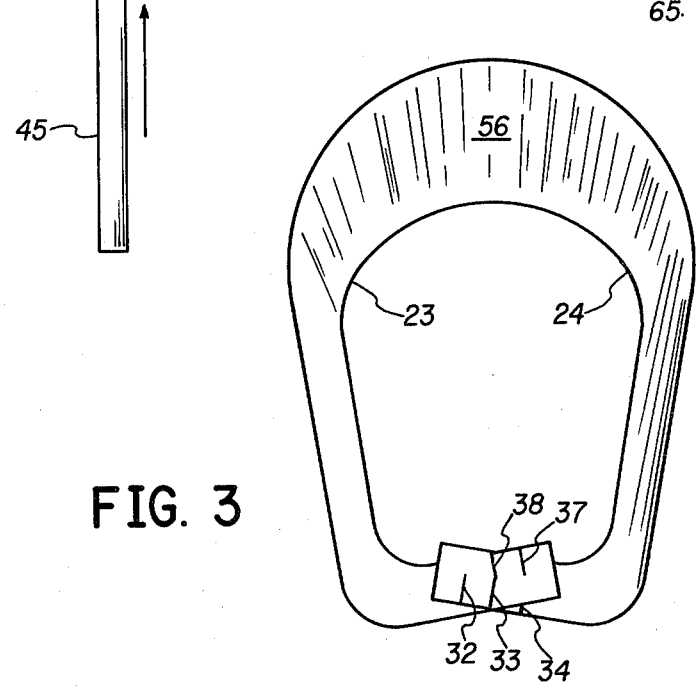
FIG. 2
FIG. 3

ARTICLE FOR MAKING A SUN VISOR AND FAN

BACKGROUND OF THE INVENTION

1. Field of the Invention

This invention relates to an article of manufacture for use in the convenient making of a fan and sun visor.

2. Description of the Prior Art

There are many instances, especially in outdoor or semioutdoor sporting events in which spectators find useful sun visors and hand fans. Often, for example, at many sporting events spectators use programs or other available magazines for fans.

SUMMARY OF THE INVENTION

In view of the above, it is an object of this invention to provide an article of manufacture which can be used to conveniently make a fan and sun visor for use, for example, at sporting events and such.

In a broad aspect, the invention is an article of manufacture, and includes a generally rectangular piece of paper having rounded corners. The piece of paper has interior perforations defined in a generally rectangular shaped interior portion with rounded corners to enable the interior portion to be torn from said rectangular piece of paper to form a fan. The interior portion has at least two holes to receive a stick for convenience in holding the fan. The portion from which the interior is removed has a separating cut and a plurality of interlocking slots at a base portion thereof. Thus, when the interior rectangle defined by the perforations is separated from the piece of paper and the stick inserted into the at least two holes, the interior rectangle can be used as a fan. In addition, when the interior rectangle is removed from the piece of paper, the piece of paper remaining can be formed into a visor which can be adjusted in size upon selection of the interlocking slots.

BRIEF DESCRIPTION OF THE DRAWING

The invention is illustrated in the accompanying drawing in which:

FIG. 1 is a plan view of the article of manufacture, in accordance with the invention, with the fan engaging stick removed.

FIG. 2 is a plan view of the fan portion of the article of manufacture of FIG. 1 with the handle or stick in inserted position, and FIG. 3 is a plan view of the visor portion of the article of manufacture of FIG. 1, showing the interlocking operation of the cuts thereof.

In the various figures of the drawing, various sizes and dimensions have been distorted or exaggerated for ease of description and clarity of illustration.

DETAILED DESCRIPTION OF THE PREFERRED EMBODIMENTS

As shown in FIG. 1, the invention is an article of manufacture, generally denoted by the reference numeral 10, and includes a generally rectangular piece of paper 11. As used herein, the term "piece of paper" is intended to refer to paper of weight suitable for the intended purpose of the fan and visor hereinbelow described, and may include heavy paper, card stock, bristol board, or the like. The piece of paper 11 has generally rounded corners 13 and 14 at the bottom, as shown, and rounded corners 15 and 16 at the top. The rounded corners 15 and 16 are configured, in the embodiment illustrated, to form a generally semicircular or continuous arcuate shape to form the visor portion of the article of manufacture, as hereinbelow described.

Within the interior of the piece of paper 11, perforations 20 are provided in a closed loop where generally rectangular configuration is shown. The perforations are configured with relatively rounded corners 21 and 22 at the bottom and a semicircular or arcuate shaped top formed by the rounded corners 23 and 24, to complete the visor portion of the piece of paper 11. Along the bottom portion 28 of the piece of paper 11, a cut 30 is provided extending from the bottom 28 to the area adjacent the perforations 20. In addition, a number of cuts 32, 33, and 34 are provided along the bottom portion 28 and a corresponding number of cuts 37, 38, and 39 are provided along the perforations 20 opposite the cuts 32, 33, and 34 on the opposite side of the cut 30 to enable the visor to be adjusted in size, as described below.

In addition, at least two holes 41 and 42 are provided in the interior portion of the piece of paper 11 within the area defined by the perforations 20 to receive a stick or handle 45 for operation of the fan. Cuts 48 and 49 are provided, angularly extending from the corners of the hole 41, and, likewise, cuts 50 and 51 are provided angularly extending from corners of the hole 42 to relieve stress within the piece of paper 11 when the stick 45 is inserted as shown and described below with reference to FIG. 2.

In the use of the article of manufacture 10, the interior portion 55 can be separated from the exterior portion 56 by tearing or cutting or otherwise removing the interior portion 55 along the perforations 20 to define a generally rectangular piece of paper with rounded bottom corners and an arcuate top as shown in FIG. 2. When the stick 45 is inserted into the respective receiving holes 41 and 42, the produced assembly, denoted by the reference numeral 60, can be used conveniently as a fan. It should be noted at this point that although receiving holes or slots 41 and 42 are illustrated, the stick 45 can be attached to the interior portion 55 by other means (not shown), such as glue, staples, or other fastening means.

The outer portion 56, once the interior portion 55 has been removed therefrom, can be formed into a visor, as illustrated in FIG. 3. Thus, one of the slots 32, 33, or 34, can be interlockingly connected within one of the slots 37, 38, or 39, as shown, to form a continuous loop, as shown. When the respective slots are interlockingly connected, as shown, the visor assembly, generally denoted by the reference numeral 65, will assume an arcuate form along the vertical axis thereof for convenient use as a sun visor. As mentioned, by the appropriate selection of the particular interlocking slots 32-34 and 37-39, the size of the visor can be adjusted to accommodate various users.

It should also be noted that the interior arcuate form produced by the rounded corners 23 and 24 of the perforations, above described, can conveniently be that of approximately the form of a human head for comfort in wearing of the visor assembly 65 by the user.

It should be apparent that because the article of manufacture, in accordance with the invention, is fabricated on a single piece of paper, that any design, promotional material, or the like, can be printed on it, as desired.

Although the invention has been described and illustrated with a certain degree of particularity, it is understood that the present disclosure is made by way of example only and that numerous changes in the combination and arrangement of parts may be resorted to by those skilled in the art without departing from the spirit and the scope of the invention as hereinafter claimed.

I claim:

1. A unitary article for the making of a fan and sun visor, comprising:
    a piece of paper, and
    a handle carried upon said piece of paper,
    said piece of paper being perforated in a closed interior loop to define upon separation at said perforations a generally rectangular fan upon which said handle is carried, and a visor portion having a bill, two sides, and bottom portions,
    said bottom portion being separated by a cut therethrough and having cuts on opposite respective edges of said separating cut to enable said bottom to be interlockingly connected to form said sun visor.

2. The article of claim 1 wherein said handle is carried upon said piece of paper within at least two receiving holes in the rectangular fan defined by said perforations.

3. The article of claim 1 wherein said handle is glued to said piece of paper within at least two receiving holes in the rectangular fan defined by said perforations.

4. The article of claim 1 wherein said handle is stapled to said piece of paper within at least two receiving holes in the rectangular fan defined by said perforations.

5. The article of claim 1 wherein said piece of paper has rounded corners at the respective bottom portions and a semicircular shape along the bill portion.

6. The article of claim 1 wherein said piece of paper is of lightweight card stock.

* * * * *